(12) United States Patent
Morefield (10) Patent No.: US 9,216,215 B2
(45) Date of Patent: Dec. 22, 2015

(54) ADJUVANT SYSTEM FOR VACCINE ADJUVANT

(75) Inventor: Garry Morefield, Nazareth, PA (US)

(73) Assignee: VAXFORM LLC, Bethlehem, PA (US)

( * ) Notice: Subject to any disclaimer, the term of this patent is extended or adjusted under 35 U.S.C. 154(b) by 0 days.

(21) Appl. No.: 13/261,421

(22) PCT Filed: Sep. 27, 2011

(86) PCT No.: PCT/US2011/001661
§ 371 (c)(1),
(2), (4) Date: May 21, 2013

(87) PCT Pub. No.: WO2012/047265
PCT Pub. Date: Apr. 12, 2012

(65) Prior Publication Data
US 2013/0259900 A1    Oct. 3, 2013

Related U.S. Application Data

(60) Provisional application No. 61/387,349, filed on Sep. 28, 2010.

(51) Int. Cl.
| | | |
|---|---|---|
| *A61K 39/39* | (2006.01) | |
| *A61K 31/70* | (2006.01) | |
| *A61K 31/7004* | (2006.01) | |
| *A61K 31/7024* | (2006.01) | |
| *A61K 45/06* | (2006.01) | |
| *A61K 39/00* | (2006.01) | |

(52) U.S. Cl.
CPC ............... *A61K 39/39* (2013.01); *A61K 31/70* (2013.01); *A61K 31/7004* (2013.01); *A61K 31/7024* (2013.01); *A61K 45/06* (2013.01); *A61K 2039/55505* (2013.01); *A61K 2039/55583* (2013.01)

(58) Field of Classification Search
CPC ....... A61K 39/00; A61K 31/70; A61K 33/06; A61K 2039/00
See application file for complete search history.

(56) References Cited

U.S. PATENT DOCUMENTS

2008/0152648 A1 * 6/2008 Kretz-Rommel et al. . 424/133.1

OTHER PUBLICATIONS

Geijtenbeek, T. B., & Gringhuis, S. I. (2009). Signalling through C-type lectin receptors: shaping immune responses. Nature Reviews Immunology, 9(7), 465-479.*

Harris, J., Sharp, F. A., & Lavelle, E. C. (2010). The role of inflammasomes in the immunostimulatory effects of particulate vaccine adjuvants. European journal of immunology, 40(3), 634-638.*

De Gregorio, E., D'Oro, U., & Wack, A. (2009). Immunology of TLR-independent vaccine adjuvants. Current opinion in immunology, 21(3), 339-345.*

Cantos, G., Barbieri, C. L., Iacomini, M., Gorin, P. A., & Travassos, L. R. (1993). Synthesis of antimony complexes of yeast mannan and mannan derivatives and their effect on Leishmania-infected macrophages. Biochem. J, 289, 155-160.*

Callahan, P. M., Shorter, A. L., & Hem, S. L. (1991). The importance of surface charge in the optimization of antigen-adjuvant interactions. Pharmaceutical research, 8(7), 851-858.*

Callahan, et al., "The importance of surface charge in optimization of antigen-adjuvant interactions," Pharmaceutical Research, 8(7):851-858 (1991).

Cantos, et al., "Synthesis of antimony complexes of yeast mannan and mannan derivatives and their effect on Leishmania-infected macrophages," Biochem. J., 289:155-160 (1999).

De Gregorio, et al., "Immunology of TLR-independent vaccine adjuvants," Current Opinion in Immunology, 21:339-345 (2009).

Dillon, et al., "Induction of protective class I MHC-restricted CTL in mice by a recombinant influenza vaccine in aluminium hydroxide adjuvant," Vaccine, 10(5):309-318 (1992).

Exley, et al., "The immunobiology of aluminium adjuvants: how do they really work?," Trends in Immunology, 31:103-109 (2010).

Harris, et al., "The role of inflammasomes in the immunostimulatory effects of particulate vaccine aduvants," Eur. J. Immunol., 40:595-653 (2010).

Marrack, et al., "Towards an understanding of the adjuvant action of aluminium," Nature Reviews Immunology, 9:287-293 (2009).

Nolan, et al., "Phase I and II randomized trials of the safety and immunogenicity of a protype adjuvanted inactivated split-influenza A (H5N1) . . . ," Vaccine, 26:4160-4167 (2008).

Teunis, et al., "Signaling through C-type lectin receptors: shaping immune responses," Nature Reviews Immunology, 9:465-479 (2009).

Zeng, et al., "Protective effect of RSV subunit vaccine candidate G1F/M2 was enhanced by a HSP70-like protein in mice," Biochem. Biophysical Res. Commn., 377:495-499 (2008).

Gupta, A., et al., "Targeting cells for drug delivery: emerging applications of mannans and mannan binding lectins," J. Scientific & Industrial Research, 68:465-483 (2009).

* cited by examiner

*Primary Examiner* — Eric Olson
*Assistant Examiner* — Dale R Miller
(74) *Attorney, Agent, or Firm* — Bordner Intellectual Property Law LLC (57) ABSTRACT

The present invention provides adjuvant compositions that have improved stability, increased potency and which provide an enhanced $T_h1$ response. The present invention also provides methods of making those compositions and administration of the improved adjuvant compositions.

6 Claims, 7 Drawing Sheets

ADJUVANT SYSTEM FOR VACCINE ADJUVANT

This application is a non-provisional application which claims the benefit of U.S. Provisional Application No. 61/387,349 filed Sep. 28, 2010.

BACKGROUND OF THE INVENTION

The present invention relates to a novel adjuvant system that enhances the immune response to a broad spectrum of antigen targets. In this system aluminum adjuvants are associated (e.g., chemically linked) with ligands to C-type leptin (CTL) receptors. This system takes advantage of the efficiency of internalization by antigen presenting cells and historical safety of aluminum adjuvants and combines it with the ability of CTL receptor ligands to produce differential immune responses.

Aluminum adjuvants have a long history of safe use in human vaccines. Their adjuvant activity is thought to arise from making the antigen particulate in nature, causing irritation at the site of injection, and activation of the NALP3 inflammasome following internalization by antigen presenting cells (APCs). However, aluminum adjuvants alone are not always appropriate for a broad array of antigen targets because they typically stimulate a skewed $T_h2$ type immune response. It has been documented for various antigens that formulation with aluminum-containing adjuvants stimulates production of IgG1 antibodies, typical for a $T_h2$ response, while little or no IgG2a antibodies, typical of a $T_h1$ response, are produced.

Therefore, there is a need to provide adjuvant compositions that have improved stability, increased potency and which provide an enhanced $T_h1$ response.

SUMMARY OF THE INVENTION

The present invention provides adjuvant compositions that have improved stability, increased potency and which provide an enhanced $T_h1$ response. The present invention also provides methods of making those compositions and administration of the improved adjuvant compositions.

The present invention provides immunological compositions comprising one or more CTL receptor ligands and one or more aluminum adjuvants. The CTL receptor ligand(s) in certain preferred embodiments linked to the aluminum adjuvant(s). The CTL receptor ligand(s) can be linked by a coordinate, covalent, hydrophilic, or hydrophobic bond to the aluminum adjuvant(s). Additionally, the CTL receptor - ligand(s) can be linked through a fluoride, phosphate, sulfate, or carbonate group to the aluminum adjuvant(s).

Figure 1:
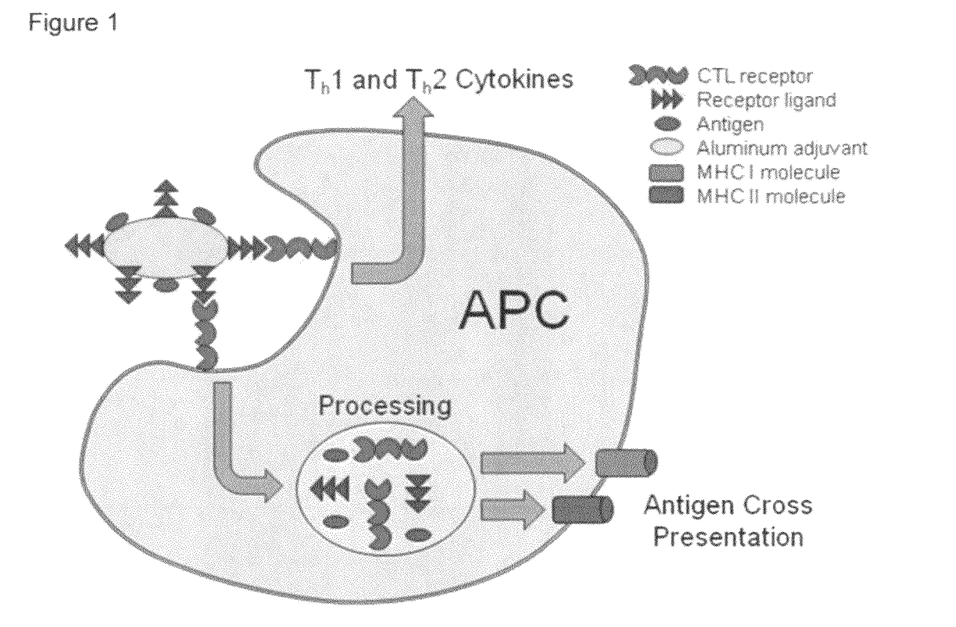

In other preferred embodiments, the CTL receptor ligand(s) comprise monosaccharides, disaccharides, or polysaccharides. In one aspect of the invention, these saccharides comprise a terminal end phosphate group or phosphodiester backbone.

In still other embodiments, the immunological compositions may further comprise one or more metallic adjuvants such as an aluminum adjuvant comprising aluminum oxy hydroxide, aluminum hydroxyphosphate, aluminum hydroxyphosphate sulfate, aluminum phosphate or combinations thereof.

The immunological compositions and adjuvant systems can be administered to an animal in combination with one or more suitable vaccines against a vaccine preventable or treatable disease. The immunological compositions and adjuvant systems can be administered to an animal in combination with suitable biological products (e.g., therapeutic proteins and/or antibodies) or small molecule drug compositions. Suitable animals include mammals (e.g., humans) and common domesticated companion animals (e.g., dogs, cats, horses, etc.) or agriculturally important animals (e.g., cows, pigs, sheep, and goats).

DESCRIPTION OF THE DRAWINGS

FIG. 1 is a schematic diagram which illustrates linkage of C-type leptin receptor ligands to aluminum adjuvants allows for receptor mediated endocytosis of co-localized antigen and adjuvant. In preferred embodiments, the endocytosis of co-localized antigen and adjuvant stimulates the production of $T_h1$ and $T_h2$ cytokines as well as targeting the antigen to endosomes where cross presentation of antigen on MCH I and II molecules can occur.

FIG. 2 is a graph illustrating that monosaccharides exhibit low adsorption to aluminum adjuvants unless modified to contain a group capable of ligand exchange binding or polymerized.

FIG. 3A is a graph illustrating that saccharides properly linked to aluminum particles remain attached to the particle even when exposed to physiological levels of phosphate in the absence of antigen.

FIG. 3B is a graph illustrating that saccharides properly linked to aluminum particles remain largely attached to the particle even when exposed to physiological levels of phosphate in the presence of antigen.

FIG. 4 is a graph illustrating the immunological compositions, formulated with an antigen targeting S.pyogenes, enhanced the production of total IgG demonstrating the potential for dose sparing.

FIG. 5 is a graph illustrating that the immunological compositions, formulated with an antigen targeting S.pyogenes, induced production of IgG2a which is indicative of a Th2 response in rats.

FIG. 6 is a graph illustrating that the immunological compositions, formulated with an antigen targeting S.pyogenes, induced production of IgG2b which is indicative of a Th1 response in rats.

DETAILED DESCRIPTION OF THE INVENTION

The present invention provides adjuvant compositions that have improved stability, increased potency and which provide an enhanced $T_h1$ response. The present invention also provides methods of making those compositions and administration of the improved adjuvant compositions C-type leptin (CTL) receptors are located on multiple cells of the immune system including macrophages, monocytes, dendritic cells, and B-cells. CTL receptors recognize various saccharides that may be produced by pathogens. Signaling through CTL receptors can induce production of cytokines resulting in the differentiation of $CD4^+$ T-cells into $T_h1$, $T_h2$, or $T_h17$ cells. Targeting of CTL receptors can also induce cross presentation of exogenous antigen on MHC I molecules and activation of $CD8^+$ T-cells resulting in a cellular immune response. It has been observed that CTL receptor agonists in a soluble presentation can dampen the immune response, while CTL receptor agonists in a particulate presentation are more suitable for enhancement of immune responses. It is contemplated that by linking CTL receptor ligands to aluminum adjuvants, the mechanism of action of both compounds can be utilized to obtain a robust immune response. The aluminum-containing adjuvant acts as a delivery particle targeting APCs and ensuring the antigen and CTL agonist are co-localized in the phagosome. The aluminum adjuvant and CTL agonist induces Th1 and Th2 cytokines as well as MHC I and II cross presentation of the co-localized antigen resulting in a robust immune response (FIG. 1)

In many instances obtaining a mixed $T_h1/T_h2$ immunological response provides more robust protection from disease compared to the $T_h2$ skewed response of traditional vaccine adjuvants such as aluminum oxyhydroxide. Advantages of the present invention include, but are not limited to, enhanced immunogenicity over traditional aluminum adjuvants while maintaining safety, the ability to stockpile, the ease of manufacture, and the low cost of goods for the adjuvant system. Activation of antigen presenting cells through multiple signaling pathways results in an enhanced immune response and the potential for dose sparing of antigen. Components of the adjuvant system are inherently stable allowing for stockpiling of the adjuvant under typical vaccine storage conditions. The nature, availability, and low cost of the raw materials for the adjuvant system allow for rapid manufacture of the adjuvant without specialized equipment. Therefore, in the case of emergency where the stockpile of adjuvant would need to be supplemented additional adjuvant could be supplied in a timely manner. This novel adjuvant system can play an integral role in enhancing the potency of vaccines to defend against biological attack or pandemic outbreaks of infectious agents.

Figure 5:
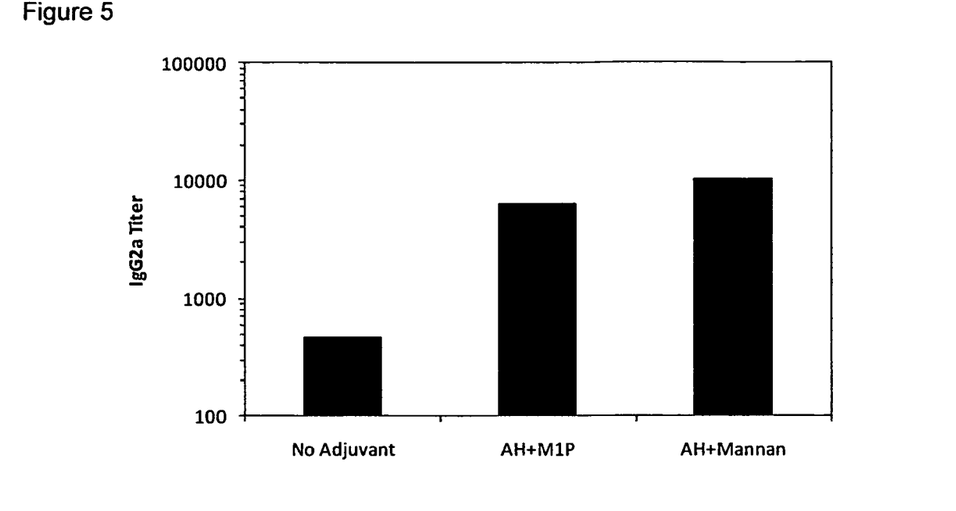
Figure 6:
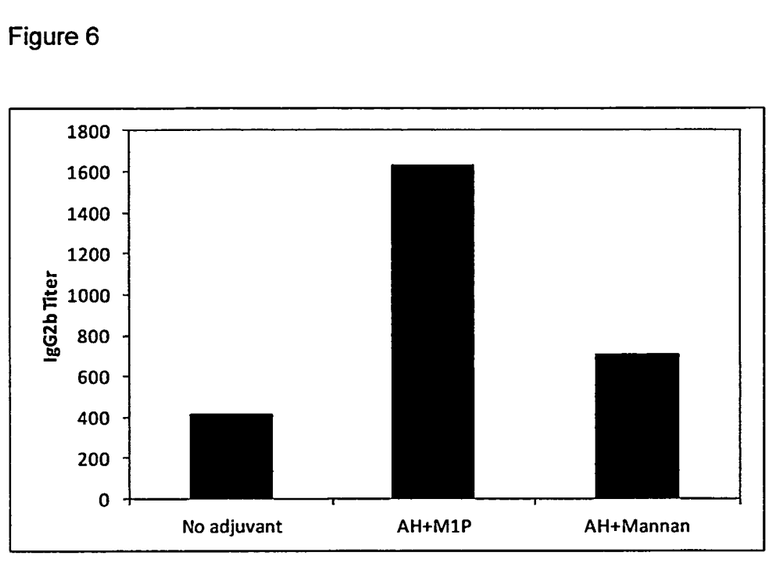

The present invention provides adjuvant compositions that provide an enhanced $T_h1$ response compared to prior art aluminum adjuvants. The combination of one or more CTL receptor agonists with one or more aluminum adjuvants where preferably the CTL receptor agonist is bound to the aluminum adjuvant increases the Th1 response relative to the aluminum adjuvant alone. The comparison of IgG2b antibodies produced by an injection of mannan bound aluminum oxyhydroxide and Spe A/B antigen, mannose-1-phosphate bound aluminum oxyhydroxide and Spe A/B antigen and aluminum oxyhydroxide without CTL receptor agonist with Spe A/B antigen when injected into rats is shown in FIG. 6. The increase in the IgG2b response in rats to the CTL receptor bound to aluminum oxyhydroxide corresponds to an increase in Th1 response as compared to the response for aluminum oxyhydroxide alone. FIG. 5 shows an increase in the IgG2a response in rats to the CTL receptor bound to aluminum oxyhydroxide as well. This corresponds to an increase in the CTL receptor bound to aluminum oxyhydroxide Th2 response as compared to the response for aluminum oxyhydroxide alone. Thus, the adjuvant compositions of the present invention provide increased antibody responses as well as increased Th2 responses when compared to aluminum adjuvants that have not been bound to CTL receptor agonists. The aluminum compound bound CTL receptor agonist adjuvants of the present invention may provide enhanced antibody titer and/or enhanced Th2 response of greater than 5%, greater than 10%, greater than 20%, greater than 30%, greater than 50%, greater than 75% or greater than 100% over aluminum adjuvant alone.

Figure 2:
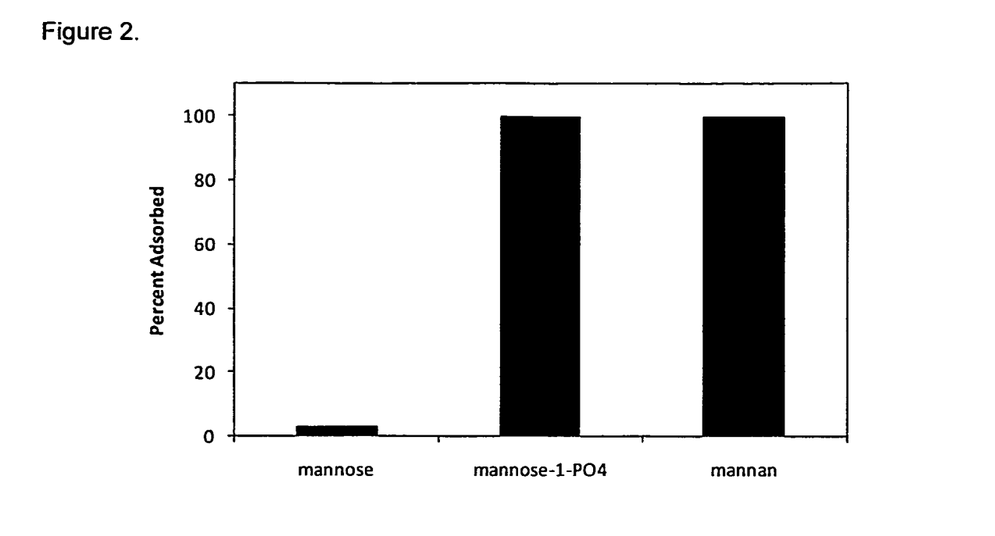

Typically small molecule CTL receptor agonists, such as monosaccharides, do not adsorb to the surface of aluminum-containing adjuvants. However, monosaccharides can be modified by a chemical group including but not limited to fluoride, phosphate, sulfate, or carbonate group which permits a ligand exchange linkage of the molecule to the aluminum-containing adjuvant. Method for modifying saccharides by addition of fluoride, phosphate, sulfate, or carbonate groups is well known in the art (Cantos, et al. Biochem. J. (1993) 289: 155-160; Carbohydrate Chemistry, Royal Society of Chemistry, Ed. R D Guthrie (1968)). This is illustrated in FIG. 2 utilizing mannose as the CTL receptor agonist and aluminum oxyhydroxide. The unmodified mannose has very little linkage to the aluminum. However, addition of a phosphate group at the 1 position of mannose (MIP) results in approximately 100% linkage of the CTL agonist to the aluminum adjuvant.

Another method to the increased avidity of the saccharide for the aluminum adjuvant particle is polymerization. For instance the avidity of the saccharide for the aluminum adjuvant particle may be increased by increasing the size of the saccharide by polymerization to produce a polysaccharide. The increase avidity for the aluminum adjuvant is due to the larger number of interactions of a polysaccharide as compared to a monosaccharide to allow for the stable linkage of the polysaccharide agonist to the aluminum adjuvant particle. In one embodiment, the physical characterization of the adjuvant system focuses on the linkage of the CTL receptor ligand to the aluminum adjuvant as well as the stability of that linkage. As seen in FIG. 2, polymerization of mannose to the polysaccharide mannan results in approximately 100% linkage of the CTL agonist to the aluminum adjuvant.

Figure 3A:
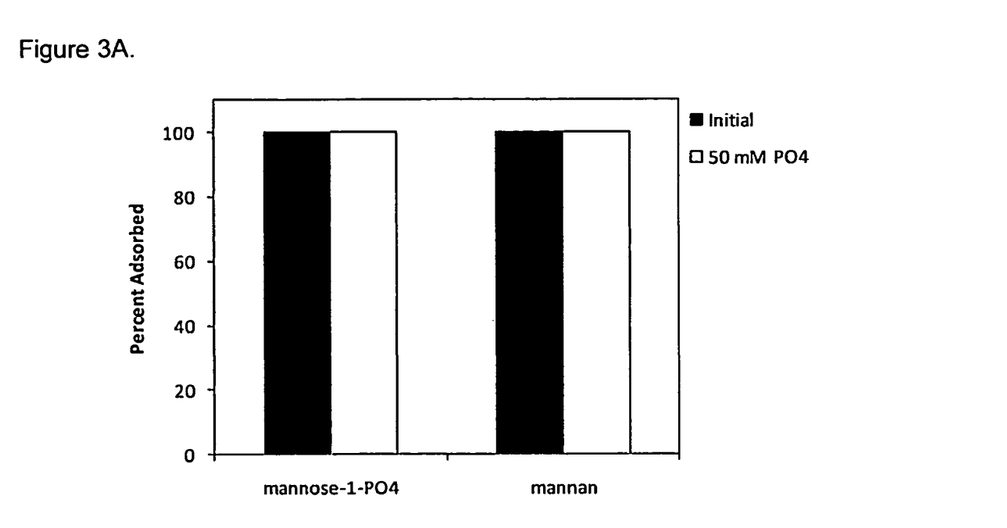
Figure 3B:
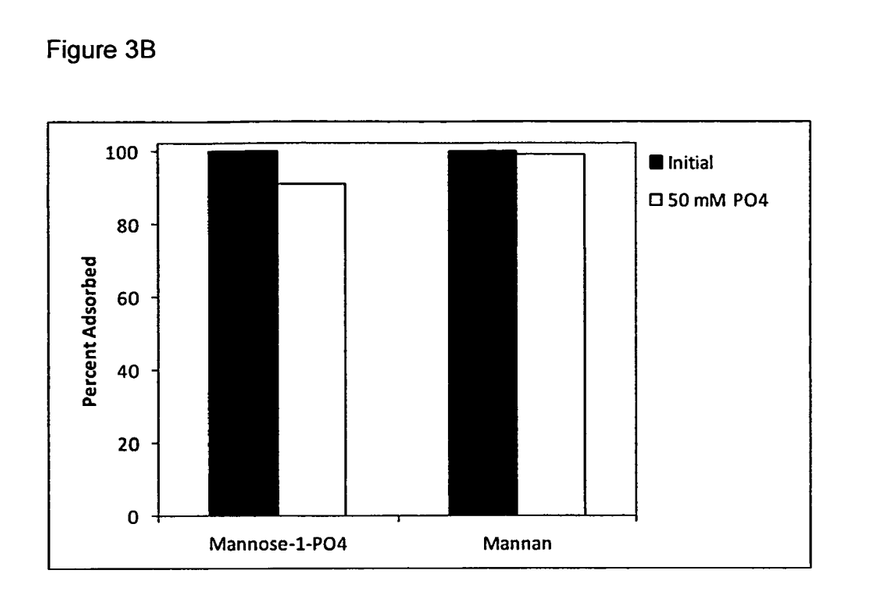

It is important to maintain the stability of the CTL agonist linkage to the aluminum particle upon exposure to body fluid following administration. Components of interstitial fluid such as phosphate, citrate, and protein have the potential to remove the linkage of the CTL agonist with aluminum-containing adjuvants. The resulting soluble CTL agonist may adversely impact the immune response. FIG. 3A illustrates that MIP as well as mannan maintain approximately 100% linkage with aluminum oxyhydroxide when exposed to 50 mM phosphate pH 7.4 for 30 minutes in the absence of antigen. FIG. 3B illustrates that M1P as well as mannan maintain a little less than 100% linkage with aluminum oxyhydroxide when exposed to 50 mM phosphate pH 7.4 for 30 minutes in the presence of antigen This demonstrates that linkage of the CTL agonist to the aluminum particle through coordinate, covalent, hydrophilic, or hydrophobic bond is suitable to maintain the association even after administration.

Antigens used in the compositions of the present invention include viral antigens such as influenza viral antigens (e.g. hemagglutinin (HA) protein, matrix 2 (M2) protein, neuraminidase), respiratory synctial virus (RSV) antigens (e.g. fusion protein, attachment glycoprotein), polio, papillomaviral (e.g. human papilloma virus (HPV), such as an E6 protein, E7 protein, L1 protein and L2 protein), Herpes Simplex, rabies virus and flavivirus viral antigens (e.g. Dengue viral antigens, West Nile viral antigens), hepatitis viral antigens including antigens from HBV and HC. Antigens used in the compositions of the present invention include bacterial antigens including those from *Streptococcus pneumonia, Haemophilus influenza, Staphylococcus aureus, Clostridium difficile* and enteric gram-negative pathogens including *Escherichia, Salmonella, Shigella, Yersinia, Klebsiella, Pseudomonas, Enterobacter, Serratia, Proteus, B.anthracis, C.tetani, B.pertussis, S.pyogenes, S.aureus, N.meningitidis* and *Haemophilus influenzea* type b. Antigens used in the compositions of the present invention include fungal antigens including those from *Candida* spp., *Aspergillus* spp., *Crytococcus neoformans, Coccidiodes* spp., *Histoplasma capsulatum, Pneumocystis carinii, Paracoccidiodes brasiliensis,*

*Plasmodium falciparum*, *Plasmodium vivax*, *Plasmodium ovale*, and *Plasmodium malariae*.

In one embodiment of the present invention the antigens of *Streptococcus pyogenes* (group A *streptococcus*, GAS) which is an important species of Gram-positive extracellular bacterial pathogen are combined in a vaccine with adjuvants of the present invention. In particular are antigens from the extracellular pyrogenic exotoxins A, B, and C. In one embodiment of the present invention Spe A/B is used as an antigen (U.S. Pat. No. 7,750,132).

In still other embodiments, the immunological compositions may further comprise one or more metallic adjuvants such as an aluminum adjuvant comprising aluminum oxy hydroxide, aluminum hydroxyphosphate, aluminum hydroxyphosphate sulfate, aluminum phosphate, alum (potassium aluminum phosphate) or combinations thereof. In addition to aluminum, other metallic salts have been used to adsorb antigens, including salts of zinc, calcium, cerium, chromium, iron, and berilium. The hydroxide and phosphate salts of aluminum are the most common.

In other preferred embodiments, the CTL receptor ligand(s) comprise monosaccharides, disaccharides, or polysaccharides. CTL receptor ligands of the present invention include saccharides which include but are not limited to Arabinose, Ribose, Ribulose, Xylose, Xylulose, Lyxose, Allose, Altrose, Fructose, Galactose, Glucose, Gulose, Idose, Mannose, Sorbose, Talose, Tagatose, Sedoheptulose, Mannoheptulose, Sucrose, Maltose, Trehalose, Lactose, Mellibiose, Amylaose, and Mannan, In one embodiment of the invention, these saccharides comprise a terminal end phosphate group or phosphodiester backbone.

Methods and schemes for administering and sufficiently dosing the immunological compositions and adjuvant systems are known within the art. The dosage and frequency (single or multiple doses) administered to a subject can vary depending upon a variety of factors, including, for example, prior exposure to an infection consequent to exposure to the antigen: health, body weight, body mass index, and diet of the subject or health-related problems. Other therapeutic regimens or agents can be used in conjunction with the methods and compositions, proteins or polypeptides of the present invention.

The immunogenic compositions for use according to the present invention may be delivered as a standard 0.5 ml injectable dose and contain from about 0.1μg to about 50μg of antigen. In a preferred embodiment of the immunogenic compositions for use according to the present invention is a standard 0.5 ml injectable dose and contains from about 3μg to about 20μg of antigen. The vaccine volume may be between 0.25 and 1.0 ml, suitably between 0.5 ml and 1.0 ml, in particular a standard 0.5ml. A vaccine dose according to the present invention may be provided in a smaller volume than conventional dosing. Low volume doses according to the present invention are suitably below 0.5 ml, typically below 0.3 ml and usually not less than 0.1 ml.

The compositions of the present invention can be administered alone or as admixtures with conventional excipients, for example, pharmaceutically, or physiologically, acceptable organic, or inorganic carrier substances suitable for enteral or parenteral application which do not deleteriously react with the composition. Suitable pharmaceutically acceptable carriers inclue water, salt solutions (such as Ringer's solution), alcohols, oils, gelatins and carbohydrates such as lactose, amylose or starch, fatty acid esters, hydroxymethylcellulose, and polyvinyl pyrolidine. Such preparations can be sterilized and, if desired, mixed with auxiliary agents such as lubricants, preservatives, stabilizers, wetting agents, emulsifiers, salts for influencing osmotic pressure, buffers, coloring and/or aromatic substances and the like which do not deleteriously react with the compositions administered to the human. Preferred diluents for diluting the vaccines of the present invention include but are not limited to 150mM NaCl with histidine and trehalose.

The determination of the appropriate amount of adjuvant combined with the CTL receptor ligand will depend on a variety of factors including the type of adjuvant, CTL receptor ligand as well as the antigen in the formulation. In fact, the amount of absorptive capacity of the CTL receptor ligand used will define the upper limit of the amount of adjuvant that can be absorbed. In the compositions and methods of the present invention the amount of saccharide to adjuvant may be in the range of about 1.5 mg of saccharide/1 mg adjuvant to about 0.05 mg of saccharide/1 mg adjuvant. In other embodiments of the compositions and methods of the present invention the amount of saccharide to adjuvant may be in the range of about 1.25 mg of saccharide/1 mg adjuvant to about 0.05 mg of saccharide/1 mg adjuvant about 1.0 mg of saccharide/1 mg adjuvant to about 0.05 mg of saccharide/1 mg adjuvant or about 1.0 mg of saccharide/1 mg adjuvant to about 0.05 mg of saccharide/1 mg adjuvant, or about 0.5 mg of saccharide/1 mg adjuvant to about 0.05 mg of saccharide/1 mg adjuvant or about 1.5 mg of saccharide/1 mg adjuvant to about 0.10 mg of saccharide/1 mg adjuvant or about 1.5 mg of saccharide/1 mg adjuvant to about 0.25 mg of saccharide/1 mg adjuvant or about 1.5 mg of saccharide/1 mg adjuvant to about 0.50 mg of saccharide/1 mg adjuvant or about 1.5 mg of saccharide/1 mg adjuvant to about 0.75 mg of saccharide/1 mg adjuvant.

The determination of the appropriate amount of antigen combined with the adjuvant/CTL receptor ligand will depend on a variety of factors including the type of adjuvant, CTL receptor ligand as well as the antigen in the formulation. In the compositions and methods of the present invention the amount of saccharide/adjuvant to antigen may be in the range of about 1.5 mg of saccharide/adjuvant per 1 mg of antigen to about 0.05 mg of saccharide/adjuvant per 1 mg of antigen. In other embodiments of the compositions and methods of the present invention the amount of saccharide to adjuvant may be in the range of about 1.25 mg of saccharide/adjuvant per 1 mg antigen to about 0.05 mg of saccharide/adjuvant per 1 mg antigen or about 1.0 mg of saccharide/adjuvant per 1 mg antigen to about 0.05 mg of saccharide/adjuvant per 1 mg antigen or about 1.0 mg of saccharide/adjuvant per 1 mg antigen to about 0.05 mg of saccharide/adjuvant per 1 mg antigen or about 0.5 mg of saccharide/adjuvant per 1 mg antigen to about 0.05 mg of saccharide/adjuvant per 1 mg antigen or about 1.5 mg of saccharide/adjuvant per 1 mg antigen to about 0.10 mg of saccharide/adjuvant per 1 mg antigen or about 1.5 mg of saccharide/adjuvant per 1 mg antigen to about 0.25 mg of saccharide/adjuvant per 1 mg antigen or about 1.5 mg of saccharide/adjuvant per 1 mg antigen to about 0.50 mg of saccharide/adjuvant per 1 mg antigen or about 1.5 mg of saccharide/adjuvant per 1 mg antigen to about 0.75 mg of saccharide/adjuvant per 1 mg antigen.

EXAMPLE 1

Vaccine Formulations

Vaccine compositions were formulated as described in Table 1.

TABLE 1

| Vaccine formulations | |
|---|---|
| Lot # | Formulation |
| 11VF001 | 100 µg SpeA/B, 20 mM Tris, 130 mM NaCl |
| 11VF002 | 100 µg SpeA/B, 20 mM Tris, 130 mM NaCl, 1.7 mg/ml AH |
| 11VF003 | 100 g SpeA/B, 20 mM Tris, 130 mM NaCl, 1.7 mg/ml AH, 300 µg/ml mannose-1-P |
| 11VF005 | 100 µg SpeA/B, 20 mM Tris, 130 mM NaCl, 1.7 mg/ml AH, 300 μg/ml mannan |
| 11VF007 | 20 mM Tris, 130 mM NaCl, 1.7 mg/ml AH, 300 μg/ml mannose-1-P |
| 11VF008 | 20 mM Tris, 130 mM NaCl, 1.7 mg/ml AH, 300 μg/ml mannan |

TABLE 2

| components of Formulation 11VF003 | | |
|---|---|---|
| Components | Concentration | Quantity |
| Spe A/B | 1.9 mg/ml | 0.297 ml |
| alhydrogel | 10 mg/ml | 0.383 ml |
| Mannose-1-phosphate | 4 mg/ml | 0.169 ml |
| Tris buffer | 50 mM | 0.714 ml |
| NaCl | 1M | 0.293 ml |
| Water | — | 0.394 ml |
| Total | | 2.25 ml |

Water, tris and alhydrogel were placed into a 15 ml tube and mixed with a vortex mixer. Spe A/B was added into the 15 ml tube and mixed by vortexing. The mixture was incubated at room temperature for 30 minutes. Mannose-1-phosphate was added followed by the addition of 1M NaCl. The entire mixture was mixed by vortexing and the mixture was incubated for 30 minutes at room temperature.

TABLE 3

| components of Formulation 11VF005 | | |
|---|---|---|
| Components | Concentration | Quantity |
| Spe A/B | 1.9 mg/ml | 0.297 ml |
| alhydrogel | 10 mg/ml | 0.383 ml |
| Mannan | 4 mg/ml | 0.169 ml |
| Tris buffer | 50 mM | 0.714 ml |
| NaCl | 1M | 0.293 ml |
| Water | — | 0.394 ml |
| Total | | 2.25 ml |

Water, tris and alhydrogel were placed into a 15 ml tube and mixed with a vortex mixer. Spe A/B was added into the 15 ml tube and mixed by vortexing. The mixture was incubated at room temperature for 30 minutes. Mannan was added followed by the addition of 1M NaCl. The entire mixture was mixed by vortexing and the mixture was incubated for 30 minutes at room temperature.

EXAMPLE 2

| Stability of the Vaccine Formulations | | | | | |
|---|---|---|---|---|---|
| | | Day | | | Target |
| Form. | Assay | 0 | 21 | Target | met |
| 11VF001 | Visual inspection | conform | conform | Clear, colorless, solution free of external particles | yes |
| | pH | 7.48 | 7.51 | pH between 7 and 8 | Yes |
| 11VF002 | Visual inspection | conform | conform | Uniform white, opaque suspension free of external particles | Yes |
| | pH | 7.19 | 7.14 | pH between 7 and 8 | Yes |
| | % SpeA/B adsorbed | 95% | 94% | >80% adsorbed | Yes |
| | % Spe A/B desorbed | 32% | 23% | % desorption steady over study | No |
| 11VF003 | Visual inspection | conform | conform | Uniform white, opaque suspension free of external particles | Yes |
| | pH | 7.27 | 7.21 | pH between 7 and 8 | Yes |
| | % SpeA/B adsorbed | 94% | 71% | >80% adsorbed | No |
| | % Spe A/B desorbed | 32% | 48% | % desorption steady over study | No |
| | % M1P adsorbed | 100% | 81% | >80% adsorbed | Yes |
| | % M1p desorbed | 9% | 19% | % desorption steady over study | No |
| 11VF005 | Visual inspection | conform | conform | Uniform white, opaque suspension free of external particles | Yes |
| | pH | 7.17 | 7.12 | pH between 7 and 8 | Yes |
| | % SpeA/B adsorbed | 96% | 93% | >80% adsorbed | Yes |
| | % Spe A/B desorbed | 30% | 23% | % desorption steady over study | Yes |
| | % mannan adsorbed | 100% | 100% | >80% adsorbed | Yes |
| | % mannan desorbed | 1% | 0% | % desorption steady over study | Yes |

Determination of the amount of carbohydrate in a sample was performed as described below. 50 μl of blank, standard, and sample were pipetted into the appropriate wells of a 96-well microplate. 150 μl of concentrated sulfuric acid was pipette into each well followed by pipetting of 30 μl of 5% phenol into each well. The plate was incubated at 90° C. for 5 min and then cooled to room temperature. The absorbance at 490 nm was then measured. In cases where the sample had a carbohydrate concentration greater than the highest standard, dilutions of the sample were prepared such that the results fall in the linear range of the assay.

Determination of the percent antigen absorbed in the adjuvanted formulation was performed as follows. The samples were centrifuged for 5 minutes at 10,000 rcf. Working BCA reagent was prepared and the reagents were mixed in a 50:1 ratio of A to B. 25 μl of standards and samples were pipetted in triplicate in the appropriate wells of a 96 well plate and 200 μl of BCA reagent was added to each well. The plate was incubated at 37° C. for 30 minutes and then cooled to room temperature. The absorbance of the wells in plate were read with a microplate reader at 570 nm. The antigen concentration in each sample using the standard curve.

Determination of the percent antigen desorbed in the adjuvanted formulation was performed as follows. The samples were centrifuged for 5 minutes at 10,000 rcf. The supernatant was removed and stored in a microcentrifuge tube. The pellet was resuspended in desorption buffer with an equivalent volume to the amount of supernatant removed and incubated for 30 minutes at room temperature. Working BCA reagent was prepared and reagents were mixed in a 3:1 ratio of A to B. The samples were centrifuged for 5 minutes at 10,000 rcf. 50 μl of standards and samples were pipetted in triplicate in the appropriate wells of a 96 well plate and 150 μl of BCA reagent was added to each well. The plate was incubated at 37° C. for 30 minutes and then allowed to cool to room temperature. The absorbance of the wells in the plate were measured with the microplate reader at 570 nm and the antigen concentration in each sample was calculated using the standard curve.

EXAMPLE 3

Adjuvant System Activity In Vivo

The potency of the adjuvant system was evaluated in vivo in established animal models for human pathogens.

TABLE 4

Antigen/adjuvant formulations for in vivo testing

| Lot # | Formulation | Route of delivery | Total volume |
|---|---|---|---|
| 11VF001 | 100 μg SpeA/B, 20 mM Tris, 130 mM NaCl | IM | 2.25 ml |
| 11VF002 | 100 μg SpeA/B, 20 mM Tris, 130 mM NaCl, 1.7 mg/ml AH | IM | 2.25 ml |
| 11VF003 | 100 μg SpeA/B, 20 mM Tris, 130 mM NaCl, 1.7 mg/ml AH, 300 μg/ml mannose-1-P | IM | 2.25 ml |
| 11VF005 | 100 μg SpeA/B, 20 mM Tris, 130 mM NaCl, 1.7 mg/ml AH, 300 μg/ml mannan | IM | 2.25 ml |
| 11VF007 | 20 mM Tris, 130 mM NaCl, 1.7 mg/ml AH, 300 μg/ml mannose-1-P | IM | 4 ml |
| 11VF008 | 20 mM Tris, 130 mM NaCl, 1.7 mg/ml AH, 300 μg/ml mannan | IM | 4 ml |

AH—aluminum oxyhydroxide

Formulations 11VF001-, 002, 003 and 005 were tested in rats by immunizing the rats intramuscularly or orally as described in Table 4 at day 0 and day 21. Sera was collected from the rats at day −7, day 14 and day 35 and assayed for antigen specific total IgG as well IgG2a and IgG2b.

TABLE 5

Log of Total IgG Titer for individual rats at day 14

| | Log Total IgG Titer (day 14) | | | |
|---|---|---|---|---|
| Individual | 11VF001 | 11VF002 | 11VF003 | 11VF005 |
| 1 | 4.29 | 4.67 | 4.99 | 5.27 |
| 2 | 3.66 | 4.93 | 5.17 | 5.67 |
| 3 | 3.66 | 5.25 | 5.00 | 5.48 |
| 4 | 3.64 | 4.98 | 5.04 | 5.24 |
| 5 | 3.47 | 5.31 | 5.11 | 5.10 |
| Avg | 3.74 | 5.03 | 5.06 | 5.35 |

TABLE 6

Log of Total IgG Titer for individual rats at day 35

| | Log Total IgG Titer (day 35) | | | |
|---|---|---|---|---|
| Individual | 11VF001 | 11VF002 | 11VF003 | 11VF005 |
| 1 | 6.02 | 5.88 | 6.25 | 6.09 |
| 2 | 5.77 | 6.13 | 6.34 | 6.42 |
| 3 | 5.58 | 6.24 | 6.41 | 6.23 |
| 4 | 6.05 | 6.35 | 6.39 | 6.20 |
| 5 | 5.62 | 6.24 | 6.28 | 6.28 |
| Avg | 5.81 | 6.16 | 6.33 | 6.24 |

TABLE 7

Mean Log of Total IgG Titer days 14, 35 with standard deviation

| | | Group | | | |
|---|---|---|---|---|---|
| Mean | Day | 11VF001 | 11VF002 | 11VF003 | 11VF005 |
| Log Titer | 0 | 1.70 | 1.70 | 1.70 | 1.70 |
| | 14 | 3.74 | 5.03 | 5.06 | 5.35 |
| | 35 | 5.81 | 6.16 | 6.33 | 6.24 |
| Std dev. | 14 | 0.31 | 0.26 | 0.08 | 0.22 |
| | 35 | 0.21 | 0.18 | 0.07 | 0.12 |

To determine the antibody titer the following procedure was performed. A 2 μg/ml solution of coating antigen in coating buffer was prepared. 100 ml of 2 μg/ml antigen was placed in each well of a 96 well plate and incubated for 1 hour at 37° C. The plate was washed once with 100 μl/well of washing buffer and 100 μl of blocking buffer was pipette into each well and incubate the plate for 1 hour at 37° C. Two-fold serial dilutions of the unknown sera in washing buffer were prepared. For early time points the dilution was typically a 1:50 dilution. For later time points the dilution was at 1:10, 000 or higher. The plate was washed twice with 100 μl/well of washing buffer. 100 μl of each sera dilution in duplicate was pipetted into the appropriate plate wells and incubate the plate for 1 hour at 37° C. An appropriate dilution of the detection antibody in blocking buffer was prepared. The plate was washed three times with 100 μl/well of washing buffer and 100 μl of detection antibody was pipette into each well and incubate the plate for 1 hour at 37° C. The plate was washed three times with 100 μl/well of washing buffer. An appropriate volume of TMB working reagent was prepared by combining 1 part solution A with 1 part solution B. 100 μl of TMB was pipetted into each well and incubate the plate for 15 minutes at room temperature. If the plate had not completed development the incubation time was increased in 5 minute increments until color developed. 100 µl of 3 M sulfuric acid was pipette into each well to stop the reaction and the absorbance at 450 nm was measured for each well. The titer was determined as the point of the 4 parameter best fit curve that is equivalent to twice the background absorbance.

Figure 4:
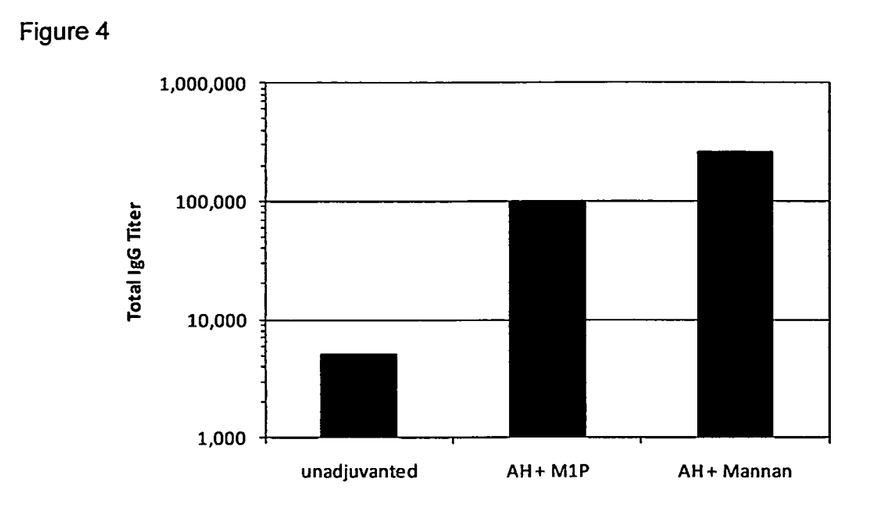

FIG. 4 illustrates that these embodiments of the adjuvant system were able to increase the total serum IgG by over one log compared to unadjuvanted antigen. This demonstrates the potential for antigen dose sparing through utilization of the adjuvant system. FIG. 5 illustrates that these embodiments of the adjuvant system enhanced the production of IgG2a antibodies. As the total IgG and IgG2a titers were not equivalent the immune response is mixed Th1/Th2 in nature. FIG. 6 illustrates that these embodiments of the adjuvant system enhanced the production of IgG2b antibodies. As the total IgG and IgG2b titers were not equivalent the immune response is mixed Th1/Th2 in nature.

Where ranges are given herein, the endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While this invention has been particularly shown and described with references to example embodiments thereof, it will be understood by those skilled in the art that the various changes in form and details may be made therein without departing from the scope of the invention encompassed by the appended claims.

Further advantages of the present immunological compositions and adjuvants of the present invention can be achieved by those skilled in the art based upon the embodiments described herein and are thus specifically within the scope of the present invention.

I claim:

1. An immunological composition comprising one or more C-type lectin (CTL) receptor ligands and one or more solid aluminum adjuvants and one or more antigens, wherein the CTL receptor ligand(s) comprise mannose-1-phospahte [or phosphorylated mannan and are] linked to the aluminum adjuvant(s) by coordinate, covalent, hydrophilic, or hydrophobic bonds.

2. The immunological composition of claim 1, wherein the aluminum adjuvant comprises aluminum oxy hydroxide, aluminum hydroxyphosphate, aluminum hydroxyphosphate sulfate, aluminum phosphate or combinations thereof.

3. The immunological composition of claim 1, wherein the aluminum adjuvant is aluminum oxyhydroxide.

4. An adjuvant comprising one or more C-type lectin (CTL) receptor ligands and one or more solid aluminum adjuvants and one or more antigens, wherein the CTL receptor ligand(s) comprise mannose-1-phospahte [or phosphorylated mannan and are] linked to the aluminum adjuvant(s) by coordinate, covalent, hydrophilic, or hydrophobic bonds.

5. The adjuvant of claim 4, wherein the aluminum adjuvant comprises aluminum oxy hydroxide, aluminum hydroxyphosphate, aluminum hydroxyphosphate sulfate, aluminum phosphate or combinations thereof.

6. The adjuvant of claim 4, wherein the aluminum adjuvant is aluminum oxyhydroxide.

* * * * *